(12) United States Patent
Pasotti et al.

(10) Patent No.: US 9,333,170 B2
(45) Date of Patent: May 10, 2016

(54) POLYVALENT POLYMERIC MATRIX FOR MODIFIED RELEASE SOLID ORAL PREPARATIONS AND METHOD OF PREPARATION THEREOF

(71) Applicant: I.P.S. International Products & Services S.r.I., San Donato Milanese (IT)

(72) Inventors: Gino Pasotti, Bologna (IT); Andrea Spalla, Segrate (IT); Ezio De Zanet, Gaggiano (IT)

(73) Assignee: I.P.S. International Products & Services S.r.l., San Donato Milanese (IT)

( * ) Notice: Subject to any disclaimer, the term of this patent is extended or adjusted under 35 U.S.C. 154(b) by 0 days.

(21) Appl. No.: 13/729,837

(22) Filed: Dec. 28, 2012

(65) Prior Publication Data

US 2013/0115282 A1 May 9, 2013

Related U.S. Application Data

(63) Continuation-in-part of application No. 12/317,427, filed on Dec. 23, 2008, now abandoned.

(30) Foreign Application Priority Data

Dec. 24, 2007 (IT) .............. 2007A002427

(51) Int. Cl.
| | | |
|---|---|---|
| *A61K 9/00* | (2006.01) | |
| *A23L 1/00* | (2006.01) | |
| *A23L 1/30* | (2006.01) | |
| *A61K 9/20* | (2006.01) | |
| *A61K 9/50* | (2006.01) | |
| *A23L 1/22* | (2006.01) | |

(52) U.S. Cl.
CPC ............. *A61K 9/0002* (2013.01); *A23L 1/0029* (2013.01); *A23L 1/22008* (2013.01); *A23L 1/30* (2013.01); *A23L 1/3008* (2013.01); *A61K 9/0095* (2013.01); *A61K 9/2081* (2013.01); *A61K 9/5026* (2013.01); *A61K 9/5042* (2013.01); *A61K 9/5063* (2013.01); *A61K 9/5073* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 3,081,233 A | * | 3/1963 | Enz et al. ................. | 424/462 |
| 5,376,382 A | * | 12/1994 | Goede ................. | A61K 9/1652 |
| | | | | 424/451 |
| 6,120,491 A | | 9/2000 | Kohn et al. | |
| 2006/0159742 A1 | * | 7/2006 | Wilson ................. | A61K 9/1652 |
| | | | | 424/451 |
| 2009/0162428 A1 | * | 6/2009 | Pasotti ................ | A23L 1/22008 |
| | | | | 424/451 |

FOREIGN PATENT DOCUMENTS

| | | |
|---|---|---|
| WO | 2007019540 A2 | 2/2007 |
| WO | 2007138022 A2 | 12/2007 |

OTHER PUBLICATIONS

Shay et al., Alpha-lipoic acid as a dietary supplement: Molecular mechanisms and therapeutic potential, Biochim Biophys Acta., Oct. 2009; 1790(10): 1149-1160.*

* cited by examiner

*Primary Examiner* — Carlos Azpuru
*Assistant Examiner* — Casey Hagopian
(74) *Attorney, Agent, or Firm* — Dilworth & Barrese, LLP

(57) ABSTRACT

A polymeric matrix for oral administration with modified release and taste masking properties is disclosed, obtained without using inert supports such as sugar spheres, comprising particles of active substance directly and individually covered with a release regulating membrane. Use of such a matrix to prepare various administration forms for oral use as well as the method of its preparation are also disclosed.

15 Claims, No Drawings

POLYVALENT POLYMERIC MATRIX FOR MODIFIED RELEASE SOLID ORAL PREPARATIONS AND METHOD OF PREPARATION THEREOF

CROSS-REFERENCE TO RELATED APPLICATION(S)

The present application is a continuation-in-part application of co-pending U.S. application Ser. No. 12/317,427 filed Dec. 23, 2008, the contents of which are incorporated by reference herein.

FIELD OF THE INVENTION

The present invention relates to a polymeric polyvalent matrix, suitable for the oral administration of modified release solid products and the related method of its production.

BACKGROUND OF THE INVENTION

The traditional systems to obtain forms of oral administration of medicaments or food supplements with modified release comprise the preparation of tablets, capsules, pellets, granulates that once swallowed release the active substance in the gastrointestinal tract according to predeterminated modes.

This release is obtained, in the case of pellets and granulates by application of the active substance on an inert core and, in the case of tablets, forming a compressed conglomerate of active principle mixed with inert components (such as binding agents and the like) and then covering the whole with one or more layers of outer membranes comprising substances adapted to provide the desired modified release, that can be a controlled, retarded, extended release according to the substances used for the cover membranes.

In this way the traditional so-called microgranules, pellets or minipellets, tablets or minitablets according to their size are obtained.

However these systems inevitably have some drawbacks, mainly due to the necessity of adding inert ingredients (such as support cores available on the market, known as sugar spheres) to the active substance. Therefore for the administration of the required dosage, the volume of the final administration form must be increased, with relevant swallowing difficulties, more particularly for high dosages, or the total dosage must be divided into several unitary doses.

SUMMARY OF THE INVENTION

The present invention solves brilliantly and surprisingly the above mentioned problems, with the revolutionary provision of a polyvalent matrix comprising an agglomerate formed by particles of active substance, directly and individually covered by one or more layers of polymeric membranes having such characteristics as to keep the active substance fully isolated from the outer environment and to adjust the release according to predeterminated modes, thus totally removing the need of an inert support core. In particular, particles of the active ingredient alone are directly coated, eliminating need for an inert inner core.

In this way such a matrix can attain final dosage forms with an active substance titer much higher than the conventional microgranules, pellets and minipellets, tablets and minitablets, thus allowing to make final administration forms with much higher dosages and better possibility to add other active substances, avoiding to make recourse to divide the total dosage into several unitary doses.

This matrix has a polyvalent function as well, because it allows to make innovative administration forms of solid oral products, such as high dosage tablets, even fractionable, without altering the modified release characteristics (as it happens with the traditional retard tablets), thus allowing to obtain an optimal flexibility of the unitary dosages to be administered.

These inventive tablets can also be crumbled, in case of swallowing difficulties, in a spoon or directly in the oral cavity and then swallowed with a minimal amount of water or other liquids.

Moreover the matrix in the formulation of disintegrating tablets, to be considered as a mere container or proportioner of the modified release active substance and not as a traditional tablet, allows also to obtain extemporaneous suspensions with a great dosage variety, by disintegrating for instance half tablet=200 mg; one tablet=400 mg; one and a half tablet=600 mg and so forth, in any suitable liquid, and then swallowing the active substance, whose modified release characteristics were not affected, in the form of a homogeneous suspension, very suitable for geriatric and pediatric use.

Moreover the same matrix of the present invention, when used in its simplest form of agglomerate of particles of active substance directly covered with one or more layers of polymeric membrane, allows to make other final dosage forms such as hard gelatine capsules, single dose sachets, oral soluble sachets, single dose bottles with metering stopper.

All the above mentioned forms of dosage cause the active substance to reach promptly after the administration the gastrointestinal tract starting the modified release, at the stomach and/or intestine level according to the properties of the used membrane and in view of the particular characteristics of fine and flowable particle size, the active substance spreads in a quick and uniform way on the whole surface of the gastrointestinal tract.

Coating each single micronized powder particle of active ingredient with a membrane allows direct administration of the product where the membrane provides taste-masking and smooth flow of the product down to the stomach, in addition to higher available dosage of each single administration form. Eliminating need for inner inert cores also avoids accidentally administering loose granules which cause swallowing difficulties in addition to taste problems. Additionally, the inventive compositions are easier to prepare than the prior art tablets, because the inventive process for preparing the same does not require any heat which would be harmful for most medicaments and food supplements. The only energy required for preparing the inventive tablets or coated granules is electrical power required for operating the requisite rotating pans, fluidized beds and screens.

DETAILED DESCRIPTION OF THE INVENTION

The positive characteristics and advantages of the inventive matrix are numerous and important for the various administration forms that can be formulated and the following may be mentioned without being limited thereto.

Whatever the final implemented form may be, such as tablets, extemporaneous preparations, oral soluble sachets, single dose bottles with metering stopper, the matrix particles forming them always show the same predeterminated characteristics of progressive, constant and gradual release by diffusion or by disintegration with time.

Even when formulated as a tablet, the matrix always covers a broad surface of the gastrointestinal tract due to the immediate tablet disintegration, with a minimal concentration of the active substance around each particle, with the above mentioned advantages in respect of the traditional tablets, even superior to pellets and minipellets, in view of the finer particle size.

The behavior of the matrix particles is not affected by the tabletting operation in view of their very reduced size and the greater pressure resistance in comparison with the traditional pellets and minipellets as well.

The tablet formulation of the matrix does not cause phenomena of surface polymerisation, that are very frequent with some low melting active ingredients such as thioctic or alpha lipoic acid, a classic problem found with traditional tablets, with consequent release interruption and modification of the retard effect. Especially preferred active ingredient is selected from thioctic acid, caffeine, choline bitartrate, potassium citrate, L-methionine and methylsulfonylmethane, while preferred coating membrane around the active granule is preferably formed from shellac, ethylcellulose, hydroxypropyl cellulose polyvinylpyrrolidone with talc and/or maize starch, e.g., in ethanol solution. Granules of capsicum, rhodiola rosea and magnesium sulfate actives can also be coated in this fashion.

Independently from the processed active substance, the matrix components have taste masking properties, thus allowing the formulation of administration forms having a direct contact with taste buds.

Flavoring or sweetening ingredients may also be added to the matrix components, so that ingestion of these final forms such as fractionable or crumbling tablets, extemporaneous suspensions, single dose sachets, single dose bottles with metering stoppers is also better palatable, with clear advantages especially in case of pediatric use.

The components of the matrix have such a specific weight, in view of their minimal size and absence of weighing down inert supports, as to allow a uniform suspension in the liquid used for the extemporaneous suspensions, single dose sachets or single bottle with metering stoppers, for the time required for its ingestion after a minimal shaking of the container, eliminating the product foot remaining in the emptied container, as it frequently happens when administering minipellets.

In particular, each granule, with the coating, is less than about 900 microns in size (including the coating), preferably less than about 800 microns in size, more preferably less than about 700 microns in size, even more preferably about 200 to about 700 microns in size, and most preferably about 600 to about 300 microns in size. Thickness of the coating itself about each granule is preferably about 100 to about 300 microns in thickness, more preferably about 100 to about 200 microns in thickness and most preferably about 100 to about 150 microns. The weight ratio of active core to coating in each granule is preferably from about 6:1 to about 1:1, more preferably from about 3:1 to about 1:1, and most preferably from about 2:1 to about 1:1.

The present invention will be explained in greater detail by way of the following examples in which the difference between the "taste masked" and "controlled release" forms of the variously-coated granules is determined by thickness and/or composition of coating about the respective granules.

Example 1

As a merely illustrative and non limiting example of the general application of the present invention, the method of preparation of a polymeric polyvalent matrix having controlled release characteristics of thioctic acid is given hereinafter, a food supplement which is well adapted to be an illustrative example.

To obtain a matrix with the mentioned characteristics it is necessary to have at disposal a starting material with a particle size between 200 and 700 μm.

The method of production to carry out direct application on the active substance of one or more layers of polymeric membrane regulating the release is as follows:

3.0 kg of a starting material having the above stated particle size is charged in a 10 L rotating pan.

While the pan is rotating, the active ingredient is covered using a 30% solution of 300 g shellac in ethanol and 300 g talc.

The covering operation may be effected continuously or in various stages until the required release rate is attained.

At the end of said operation the product is sieved with a 790 μm mesh and dusted with a 425 μm mesh.

The product is left drying in the pan for 3 hours at room temperature.

The finished product has a final titer of 880 mg/g and the release data obtained using the methodology "Dissolution test for solid oral forms" described in the European Pharmacopoeia are the following:

after 1 hour: 18.9%; after 2 hours: 36.0%; after 4 hours: 62.3%; after 8 hours: 86.9%.

The bulk density results to be between 0.3-0.5, so that the product obtained as above stated, can be blended with excipients like cellulose, maize starch, powdered flavors and others, to make a compression obtaining a tablet where the active substance is distributed homogeneously, according to the criteria set by the European Pharmacopoeia.

Invention tablets produced using a mixture of the product obtained as above and excipients by direct compression, analysed according to the above described methodology, did not show release variations, so that the method of preparation of the invention tablets is such as not to cause degradation of lipoic acid and the whole production process keeps the chemical integrity of this active substance.

Example 2

Production Process of Thioctic Acid Taste Masked

Stage 1—Selection of the Starting Material

A 630 microns net was mounted on a vibrating WESTON screen, and a container was placed under the screen orifice to collect the selected product. About 4.0 kg of thioctic acid was placed on the net, with a slight pressure in the direction of rotation. When all of the fraction <630 microns passed through the net, the fraction >630 microns was removed and placed in a container. The preceding operation was repeated until the amount of the fraction <630 microns required for the production of the lot (100.0 kg+10%) was reached.

The 630 microns net was removed and a 250 microns net was mounted on the vibrating screen, with a container placed under the screen orifice to collect the selected product. About 2.0 kg of thioctic acid was placed on the net and screened, with a slight pressure in the direction of rotation. When all the fraction <250 microns passed through the net, the product left on the net was removed and placed in a container to be stocked. The preceding operation was repeated until the amount required for the production of the lot (kg. 100.0) was reached. The fraction <250 microns was set aside.

Stage 2—Preparation of the 20.66% Coating Solution Comprising Shellac 19.83% w/w in Ethanol 96%+0.83% Polysorbate 80

14.40 kg ethanol 96% was placed in a stainless steel dissolver with a capacity of about 60 L. 3.60 kg shellac was slowly added under agitation, with agitation maintained to complete dissolution (about 2 hours). Then 0.150 kg polysorbate 80 was added, with stirring for about 10 minutes.

Stage 3—Adjustment of Flow Rate of the 20.66% Coating Solution Comprising Shellac 19.83% w/w in Ethanol 96%+0.83% Polysorbate 80

6.250 kg. of the 20.66% coating solution comprising shellac 19.83% w/w in ethanol 96%+0.83% polysorbate 80 (previously prepared, stage 2) was placed in a container. A hose connected to a membrane pump was placed in the container, with the membrane pump switched on and set to a speed at 40 rpm. A container was placed to collect the solution near the atomizer nozzle, and calibrated to conduct a delivery test of one minute (theoretical amount 250 g, range 230-270 g). If the delivered quantity was below the range, the pump revolutions were increased, and if above the range, the revolutions reduced. At the end of the test, the solution was recovered, and placed again in the container.

Stage 4—Coating Thioctic Acid with 6.250 kg of 20.66% Solution of Shellac+Polysorbate 80 w/w in Ethanol 96% and 10.0 kg of Maize Starch 100.0 kg of the fraction between 250 and 630 microns of thioctic acid starting material selected in the preceding stages was placed inside an automatic rotating pan with capacity of about 200 L. Rotation of the pan was started at a speed of 6 rpm±2 rpm, 1 kg of talc was added and rotated for 5 minutes before starting the coating operation. The pan speed was increased to 22 rpm±2 rpm, the atomizer was positioned at about 20 cm from the rotating mass and the jet directed to the left upper quadrant, with the nebulization pressure of the atomizer adjusted to 1 bar (i.e., a range 0.8-1.2. bar). 250 g of 20.66% solution of shellac+polysorbate 80 w/w in ethanol 96% was sprayed over one minute, and with 400 g of maize starch sprinkled at the end. The previous operation was repeated after about two minutes and continued in the same way until 6.250 kg of solution and 10.00 kg of maize starch are applied on the product. The product was then dried in the pan at room temperature at a speed of 6 rpm±2 rpm for 5 hours.

Stage 4a—Coating Thioctic Acid with 11.90 kg of 20.66% Solution of Shellac+Polysorbate 80 w/w in Ethanol 96% and 11.90 kg of Talc The pan was set at a speed of 22 rpm±2 rpm, the atomizer positioned at about 20 cm from the rotating mass and the jet directed to the left hand upper quadrant, with the nebulization pressure of the atomizer adjusted to 1 bar (i.e., a range 0.8-1.2 bar). 250 g of 20.66% solution of shellac+polysorbate 80 w/w in ethanol 96% was sprayed over about one minute, with 250 g of talc sprinkled at the end. After about 5 minutes, the previous operation was repeated and continued in the same way until 11.90 kg of solution and 11.90 kg of talc were applied on the product. The product was then dried in the pan at room temperature at a speed of 6 rpm±2 rpm for 5 hours.

Stage 5—Final Selection of the Obtained Product

The pan was rotated at a speed of 6 rpm±2 rpm, and 0.100 kg colloidal silicon dioxide was added, followed by rotating for 10 minutes. A 790 microns net was mounted on a WESTON vibrating screen, and a container mounted under the screen to collect the selected product. The screen was activated, with about 4.0 kg of coated thioctic acid placed on the net with a slight pressure in the direction of rotation. When all the fraction <790 microns passed through the net, the fraction >790 microns was removed and placed in a container for discarding. The preceding operation was repeated up to the end of screening to obtain the product that was then selected with a 250 microns net. The 790 microns net was removed and the 250 microns net mounted in its place on the vibrating screen, with a container placed under the screen orifice to collect the product <250 microns. The screen was activated, with about 2.0 kg of coated thioctic acid placed on the net, with slight pressure in the direction of rotation.

When all the fraction <250 microns passed through the net, the product left on the net was removed and placed in the container provided for the packaging operation. The preceding operation was repeated up to the selection end, and with the fraction <250 microns discarded. The sample was then analyzed for determining titre and in vitro release rate.

Using the analysis procedure according to Example 1 supra, it was determined the product had a dissolution rate of 77.3% after 1 hour (0.74% standard deviation) and 99.6% after 2 hours (0.42% standard deviation).

Example 3

Production Process of Thioctic Acid Taste Masked with Ethylcellulose Membrane

Stage 1—Selection of the Starting Material

A 630 microns net was mounted on a vibrating WESTON screen, with a container placed under the screen to collect the selected product. About 4.0 kg of thioctic acid was placed on the net, with a slight pressure in the direction of rotation. When all of the fraction <630 microns passed through the net, the fraction >630 microns was removed and placed in a container. The preceding operation was repeated until the amount required for the production of the lot (100.0 kg+10%) was reached.

The 630 microns net was removed and a 250 microns net was mounted on the vibrating screen, with a container placed under the screen orifice to collect the selected product. About 2.0 kg of thioctic acid was placed on the net and screened, with a slight pressure in the direction of rotation. When all the fraction <250 microns passed through the net, the product left on the net was removed and placed in a container to be stocked. The preceding operation was repeated until the amount required for the production of the lot (kg. 100.0) was reached. The fraction <250 microns was set aside.

Stage 2—Preparation of the Coating Solution Comprising Ethylcellulose 5% w/w in Ethanol 96%

19.00 kg ethanol 96% was placed in a stainless steel dissolver with a capacity of about 60 L. 1.00 kg. ethylcellulose N 100, was slowly added, with agitation maintained to complete dissolution (about 4 hours). Then, the obtained solution was stored in a container.

Stage 3—Adjustment of Flow Rate of the Coating Solution Comprising Ethylcellulose 5% w/w in Ethanol 96%

The ethylcellulose solution was placed in a container. A hose connected to a membrane pump was placed in the container, with the membrane pump switched on and set to a speed of 40 rpm. A container was placed to collect the solution near the atomizer nozzle, and calibrated to conduct a delivery test of one minute (theoretical amount 200 g, range 180-220 g). If the delivered quantity was below the range, the pump revolutions were increased, and if above the range, the revolutions reduced. At the end of the test, the solution was recovered, and placed again in the container.

Stage 4—Coating Thioctic Acid with 20 kg of Solution of 5% Ethylcellulose w/w in Ethanol 96% and 20.0 kg of Talc 100.0 kg of the fraction between 250 and 630 microns of thioctic acid starting material selected in the preceding stages was placed inside an automatic rotating pan with capacity of about 200 L. Rotation of the pan was started at a speed of 6 rpm±2 rpm, 1 kg of talc was added and rotated for 5 minutes before starting the coating operation. The pan speed was increased to 22 rpm±2 rpm, the atomizer was positioned at about 20 cm from the rotating mass and the jet directed to the left upper quadrant, with the nebulization pressure of the atomizer adjusted to 1 bar (i.e., a range 0.8-1.2. bar). 250 g of solution of ethylcellulose 5% w/w in ethanol 96% was sprayed over about one minute and fifteen seconds, and with 450 g of talc sprinkled at the end. The previous operation was repeated after about five minutes and continued in the same way until 20 kg of solution and 20 kg of talc are applied on the product. The product was then dried in the pan at room temperature at a speed of 6 rpm±2 rpm for 5 hours.

Stage 5—Final Selection of the Obtained Product

The pan was rotated at a speed of 6 rpm±2 rpm, and 0.100 kg colloidal silicon dioxide was added, followed by rotating for 10 minutes. A 790 microns net was mounted on a WESTON vibrating screen, and a container mounted under the screen to collect the selected product. The screen was activated, with about 4.0 kg of coated thioctic acid placed on the next with a slight pressure in the direction of rotation. When all the fraction <790 microns passed through the net, the fraction >790 microns was removed and placed in a container for discarding. The preceding operation was repeated up to the end of screening to obtain the obtained product, that was then selected with a 250 microns net. The 790 microns net was removed and the 250 microns net mounted in its place on the vibrating screen, with a container placed under the screen orifice to collect the product <250 microns. The screen was activated, with about 2.0 kg of coated thioctic acid placed on the net, with slight pressure in the direction of rotation.

When all the fraction <250 microns passed through the net, the product left on the net was removed and placed in the container provided for the packaging operation. The preceding operation was repeated up to the selection end, and with the fraction <250 microns discarded. The sample was then analyzed for determining titre and in vitro release rate.

Using the analysis procedure according to Example 1 supra, it was determined the product had a dissolution rate of 100.4% after 1 hour (0.61% standard deviation) and 100.7% after 2 hours (0.65% standard deviation).

Example 4

Production Process of Thioctic Acid Controlled Release with Shellac Membrane

Stage 1—Selection of the Starting Material

A 630 microns net was mounted on a vibrating WESTON screen, with a container placed under the screen orifice to collect the selected product. About 4.0 kg of thioctic acid was placed on the net, with a slight pressure in the direction of rotation. When all of the fraction <630 microns passed through the net, the fraction >630 microns was removed and placed in a container. The preceding operation was repeated until the amount required for the production of the lot (100.0 kg+10%) was reached.

The 630 microns net was removed and a 250 microns net was mounted on the vibrating screen, with a container placed under the screen orifice to collect the selected product. About 2.0 kg of thioctic acid was placed on the net and screened, with a slight pressure in the direction of rotation. When all the fraction <250 microns passed through the net, the product left on the net was removed and placed in a container to be stocked. The preceding operation was repeated until the amount required for the production of the lot (kg. 100.0) was reached. The fraction <250 microns was set aside.

Stage 2—Preparation of the 20.83% Coating Solution Comprising Shellac 30% w/w in Ethanol 96%

19.46 kg ethanol 96% was placed in a stainless steel dissolver with a capacity of about 60 L. 8.34 kg shellac was slowly added under agitation, with agitation maintained to complete dissolution (about 4 hours).

Stage 3—Adjustment of Flow Rate of the 20.83% Coating Solution Comprising Shellac 30% w/w in Ethanol 96%

17.0 kg. of the 20.83% coating solution comprising shellac 30% w/w in ethanol 96% (previously prepared, stage 2) was placed in a container. A hose connected to a membrane pump was placed in the container, with the membrane pump switched on and set to a speed at 40 rpm. A container was placed to collect the solution near the atomizer nozzle, and calibrated to conduct a delivery test of one minute (theoretical amount 200 g, range 180-220 g). If the delivered quantity was below the range, the pump revolutions were increased, and if above the range, the revolutions reduced. At the end of the test, the solution was recovered, and placed again in the container.

Stage 4—Coating Thioctic Acid with 17.0 kg of Solution of Shellac 30% w/w in Ethanol 96% and 17.0 kg of Talc 100.0 kg of the fraction between 250 and 630 microns of thioctic acid starting material selected in the preceding stages was placed inside an automatic rotating pan with capacity of about 200 L. Rotation of the pan was started at a speed of 6 rpm±2 rpm, 0.8 kg of talc was added and rotated for 5 minutes before starting the coating operation. The pan speed was increased to 22 rpm±2 rpm, the atomizer was positioned at about 20 cm from the rotating mass and the jet directed to the left upper quadrant, with the nebulization pressure of the atomizer adjusted to 1 bar. 400 g of solution of shellac 30% w/w in ethanol 96% was sprayed over about two minutes, and with 400 g of talc sprinkled at the end. The previous operation was repeated after about two minutes and continued in the same way until 17 kg of solution and 17 kg of talc are applied on the product. The product was then dried in the pan at room temperature at a speed of 6 rpm±2 rpm for 5 hours.

Stage 5—Final Selection of the Obtained Product

The pan was rotated at a speed of 6 rpm±2 rpm, and 0.100 kg colloidal silicon dioxide was added, followed by rotating for 10 minutes. A 790 microns net was mounted on a WESTON vibrating screen, and a container mounted under the screen to collect the selected product. The screen was activated, with about 4.0 kg of coated thioctic acid placed on the net with a slight pressure in the direction of rotation. When all the fraction <790 microns passed to through the net, the fraction >790 microns was removed and placed in a container for discarding. The preceding operation was repeated up to the end of screening to obtain the obtained product, that was then selected with a 250 microns net. The 790 microns net was removed and the 250 microns net mounted in its place on the vibrating screen, with a container placed under the screen orifice to collect the product <250 microns. The screen was activated, with about 2.0 kg of coated thioctic acid placed on the net, with slight pressure in the direction of rotation.

When all the fraction <250 microns passed through the net, the product left on the net was removed and placed in the container provided for the packaging operation. The preceding operation was repeated up to the selection end, and with the fraction <250 microns discarded. The sample was then analyzed for determining titre and in vitro release rate.

Using the analysis procedure according to Example 1 supra, it was determined the product had a dissolution rate of 19.6% after 1 hour (0.00% standard deviation), 42.5% after 2 hours (2.28% standard deviation), 2.7% after 4 hours (0.34% standard deviation) and 95.6% after 8 hours (0.16% standard deviation).

Example 5

Production Process of Thioctic Acid Controlled Release with Ethylcellulose Membrane Stage 1—Selection of the Starting Material A 630 microns net was placed on a vibrating WESTON screen, with a container placed under the screen orifice to collect the selected product. About 4.0 kg of thioctic acid was placed on the net, with a slight pressure in the direction of rotation. When all of the fraction <630 microns passed through the net, the fraction >630 microns was removed and placed in a container. The preceding operation was repeated until the amount required for the production of the lot (100.0 kg+10%) is reached.

The 630 microns net was removed and a 250 microns net was mounted on the vibrating screen, with a container placed under the screen orifice to collect the selected product. About 2.0 kg of thioctic acid was placed on the net and screened, with a slight pressure in the direction of rotation. When all the fraction <250 microns passed through the net, the product left on the net was removed and placed in a container to be stocked. The preceding operation was repeated until the amount required for the production of the lot (kg. 100.0) was reached. The fraction <250 microns was set aside.

Stage 2—Preparation of the Coating Solution Comprising Ethylcellulose 5% w/w in Ethanol 96%

34.20 kg ethanol 96% was placed in a stainless steel dissolver with a capacity of about 60 L. 1.8 kg. ethylcellulose N 100, was slowly added, with agitation maintained to complete dissolution (about 4 hours). Then, the obtained solution was stored in a container.

Stage 3—Adjustment of Flow Rate of the Coating Solution Comprising Ethylcellulose 5% w/w in Ethanol 96%

26.0 kg. of the ethylcellulose solution prepared above was placed in a container. A hose connected to a membrane pump was placed in the container, with the membrane pump switched on and set to a speed at 40 rpm. A container was placed to collect the solution near the atomizer nozzle, and calibrated to conduct a delivery test of one minute (theoretical amount 200 g, range 180-220 g). If the delivered quantity was below the range, the pump revolutions were increased, and if above the range, the revolutions reduced. At the end of the test, the solution was recovered, and placed again in the container.

Stage 4—Coating Thioctic Acid with 17.0 kg of Solution of 5% Ethylcellulose w/w in Ethanol 96% and 26.0 kg of Talc 100.0 kg of the fraction between 250 and 630 microns of thioctic acid starting material selected in the preceding stages was placed inside an automatic rotating pan with capacity of about 200 L. Rotation of the pan was started at a speed of 6 rpm±2 rpm, 0.8 kg of talc was added and rotated for 5 minutes before starting the coating operation. The pan speed was increased to 22 rpm±2 rpm, the atomizer was positioned at about 20 cm from the rotating mass and directed the jet to the left upper quadrant, with the nebulization pressure of the atomizer adjusted to 1 bar (i.e., a range 0.8-1.2. bar). 350 g of solution of ethylcellulose 5% w/w in ethanol 96% was sprayed over about one minute and forty five seconds, and with 350 g of talc sprinkled at the end. The previous operation was repeated after about five minutes and continued in the same way until 26 kg of solution and 26 kg of talc are applied on the product. The product was then dried in the pan at room temperature at a speed of 6 rpm±2 rpm for 5 hours. The amounts of solution of ethylcellulose 55% w/w in ethanol 96% and talc of the following coating steps are decided as a function of the analysis results.

Stage 5—Final Selection of the Obtained Product

The pan was rotated at a speed of 6 rpm±2 rpm, and 0.100 kg colloidal silicon dioxide was added, followed by rotating for 10 minutes. A 790 microns net was mounted on a WESTON vibrating screen, and a container mounted under the screen to collect the selected product. The screen was activated, with about 4.0 kg of coated thioctic acid placed on the next with a slight pressure in the direction of rotation. When all the fraction <790 microns passed to the lower part of the net, the fraction >790 microns was removed and placed in a container for discarding. The preceding operation was repeated up to the end of screening to obtain the obtained product, that was then selected with a 250 microns net. The 790 microns net was removed and the 250 microns net mounted in its place on the vibrating screen, with a container placed under the screen orifice to collect the product <250 microns. The screen was activated, with about 2.0 kg of coated thioctic acid placed on the net, with slight pressure in the direction of rotation.

When all the fraction <250 microns passed through the net, the product left on the net was removed and placed in the container provided for the packaging operation. The preceding operation was repeated up to the selection end, and with the fraction <250 microns discarded. The sample was then analyzed for determining titre and in vitro release rate.

Using the analysis procedure according to Example 1 supra, it was determined the product had a dissolution rate of 24.1% after 1 hour (7.22% standard deviation), 39.8% after 2 hours (1.86% standard deviation), 69.2% after 4 hours (6.23% standard deviation) and 95.2% after 8 hours (1.00% standard deviation).

Example 6

Production Process of Caffeine Taste Masked with Shellac Membrane

Stage 1—Selection of the Starting Material

A 250 microns net was mounted on a vibrating Weston screen, with a container placed under the screen orifice to collect the selected product. About 2.0 kg of caffeine was placed on the net and screened, with a slight pressure in the direction of rotation. When all the fraction <250 microns passed through the net, the product left on the net was removed and placed in a container to be stocked. The preceding operation was repeated until the amount required for the production of the lot (kg. 100.0) was reached. The fraction <250 microns was set aside.

Stage 2—Preparation of the Coating Solution Comprising Shellac 30% w/w in Ethanol 96%

20.3 kg ethanol 96% was placed in a stainless steel dissolver with a capacity of about 60 L. 3.60 kg of shellac was slowly added under agitation, with agitation maintained to complete dissolution (about 2 hours). The obtained solution was loaded into containers.

Stage 3—Adjustment of Flow Rate of the Coating Solution Comprising Shellac 30% w/w in Ethanol 96%

A hose connected to a membrane pump was placed in the container containing the shellac solution, with a membrane pump switched on and set to a speed at 40 rpm. A container was placed to collect the solution near the atomizer nozzle, and calibrated to conduct a delivery test of one minute (theoretical amount 250 g, range 230-270 g). If the delivered quantity was below the range, the pump revolutions were increased, and if above the range, the revolutions reduced. At the end of the test, the solution was recovered, and placed again in the container.

Stage 4—Coating Caffeine with 29.0 kg of Solution of Shellac 30% w/w in Ethanol 96% and 19.0 kg of Talc 72.0.0 kg of the fraction between 250 and 630 microns of caffeine starting material selected in the preceding stages was placed inside an automatic rotating pan with capacity of about 200 L. Rotation of the pan was started at a speed of 6 rpm±2 rpm, 1 kg of talc was added and rotated for 5 minutes before starting the coating operation. The pan speed was increased to 22 rpm±2 rpm, the atomizer was positioned at about 20 cm from the rotating mass and directed the jet to the left upper quadrant, with the nebulization pressure of the atomizer adjusted to 1 bar (i.e., a range 0.8-1.2. bar). 250 g of shellac 30% w/w in ethanol 96% was sprayed over one minute and 15 seconds, and with 164.0 g of talc sprinkled at the end. The previous operation was repeated after about two minutes and continued in the same way until 29.0 kg of solution and 19.0 kg of talc are applied on the product. The product was then dried in the pan at room temperature at a speed of 6 rpm±2 rpm for 5 hours.

Stage 5—Final Selection of the Obtained Product

The pan was rotated at a speed of 6 rpm±2 rpm, and 0.070 kg colloidal silicon dioxide was added, followed by rotating for 10 minutes. A 790 microns net was mounted on a WESTON vibrating screen, and a container mounted under the screen to collect the selected product. The screen was activated, with about 4.0 kg of coated caffeine placed on the net with a slight pressure in the direction of rotation. When all the fraction <790 microns passed to the lower part of the net, the fraction >790 microns was removed and placed in a container for discarding. The preceding operation was repeated up to the end of screening to obtain the obtained product, that was then selected with a 250 microns net. The 790 microns net was removed and the 250 microns net mounted in its place on the vibrating screen, with a container placed under the screen orifice to collect the product <250 microns. The screen was activated, with about 2.0 kg of coated caffeine placed on the net, with slight pressure in the direction of rotation.

When all the fraction <250 microns passed through the net, the product left on the net was removed and placed in the container provided for the packaging operation. The preceding operation was repeated up to the selection end, and with the fraction <250 microns discarded. The sample was then analyzed for determining titre and in vitro release rate.

Using the analysis procedure according to Example 1 supra, it was determined the product had a dissolution rate of 96.0% after 1 hour (1.63% standard deviation) and 96.5% after 2 hours (1.38% standard deviation).

Example 7

Production Process of Caffeine Taste Masked with Ethylcellulose Membrane

Stage 1—Selection of the Starting Material

A 250 microns net was mounted on a vibrating WESTON screen mount, and a container was placed under the screen orifice to collect the selected product. About 2.0 kg of caffeine was placed on the net, with a slight pressure in the direction of rotation. When all of the fraction <250 microns passed through the net, the fraction >250 microns was removed and placed in a container. The preceding operation was repeated until the amount required for the production of the lot (100.0 kg) was reached. The fraction <250 microns was set aside.

Stage 2—Preparation of the Coating Solution Comprising Ethylcellulose 5% w/w in Ethanol 96%

19.00 kg ethanol 96% was placed in a stainless steel dissolver with a capacity of about 60 L. 1.00 KG. ethylcellulose N 100, was slowly added, with agitation maintained to complete dissolution (about 4 hours). Then, the obtained solution was stored in a container.

Stage 3—Adjustment of Flow Rate of the Coating Solution Comprising Ethylcellulose 5% w/w in Ethanol 96%

The 5% ethylcellulose solution was placed in a container. A hose connected to a membrane pump was placed in the container, with the membrane pump switched on and set to a speed at 40 rpm. A container was placed to collect the solution near the atomizer nozzle, and calibrated to conduct a delivery test of one minute (theoretical amount 200 g, range 180-220 g). If the delivered quantity was below the range, the pump revolutions were increased, and if above the range, the revolutions reduced. At the end of the test, the solution was recovered, and placed again in the container.

Stage 4—Coating Caffeine with 20 kg of Solution of 5% Ethylcellulose w/w in Ethanol 96% and 18.0 kg of Talc 100.0 kg of the fraction between 250 and 630 microns of caffeine starting material selected in the preceding stages was placed inside an automatic rotating pan with capacity of about 200 L. Rotation of the pan was started at a speed of 6 rpm±2 rpm, 1 kg of talc was added and rotated for 5 minutes before starting the coating operation. The pan speed was increased to 22 rpm±2 rpm, the atomizer was positioned at about 20 cm from the rotating mass and the jet directed to the left upper quadrant, with the nebulization pressure of the atomizer adjusted to 1 bar (i.e., a range 0.8-1.2. bar). 250 g of solution of ethylcellulose 5% w/w in ethanol 96% was sprayed over about one minute and fifteen seconds, and with 225 g of talc sprinkled at the end. The previous operation was repeated after about five minutes and continued in the same way until 20 kg of solution and 18 kg of talc were applied on the product. The product was then dried in the pan at room temperature at a speed of 6 rpm±2 rpm for 5 hours.

Stage 5—Final Selection of the Obtained Product

The pan was rotated at a speed of 6 rpm±2 rpm, and 0.100 kg colloidal silicon dioxide was added, followed by rotating for 10 minutes. A 790 microns net was mounted on a WESTON vibrating screen, and a container mounted under the screen to collect the selected product. The screen was activated, with about 4.0 kg of coated caffeine placed on the net with a slight pressure in the direction of rotation. When all the fraction <790 microns passed to the lower part of the net, the fraction >790 microns was removed and placed in a container for discarding. The preceding operation was repeated up to the end of screening to obtain the obtained product, that was then selected with a 250 microns net. The 790 microns net was removed and the 250 microns net mounted in its place on the vibrating screen, with a container placed under the screen orifice to collect the product <250 microns. The screen was activated, with about 2.0 kg of coated caffeine placed on the net, with slight pressure in the direction of rotation.

When all the fraction <250 microns passed through the net, the product left on the net was removed and placed in the container provided for the packaging operation. The preceding operation was repeated up to the selection end, and with the fraction <250 microns discarded.

Example 8

Production Process of Caffeine Taste Masked with Shellac Membrane

Stage 1—Selection of the Starting Material

A 250 microns net was placed on a vibrating WESTON screen, and a container placed under the screen orifice to collect the selected product. About 2.0 kg of caffeine was placed on the net, with a slight pressure in the direction of rotation. When all of the fraction <250 microns passed through the net, the fraction >630 microns was removed and placed in a container. The preceding operation was repeated until the amount required for the production of the lot (72.0 kg) was reached. The fraction <250 microns was set aside.

Stage 2—Preparation of the Coating Solution Comprising Shellac 30% w/w in Ethanol 96%

38.5 kg ethanol 96% was placed in a stainless steel dissolver with a capacity of about 60 L. 16.50 kg of shellac was slowly added under agitation, with agitation maintained to complete dissolution (about 2 hours). The obtained solution was loaded into containers.

Stage 3—Adjustment of Flow Rate of the Coating Solution Comprising Shellac 30% w/w in Ethanol 96%

A hose connected to a membrane pump was placed in the container containing the shellac solution, with a membrane pump switched on and set to a speed at 34 rpm. A container was placed to collect the solution near the atomizer nozzle, and calibrated to conduct a delivery test of one minute (theoretical amount 200 g, range 180-220 g). If the delivered quantity was below the range, increase the pump revolutions were increased, and if above the range, the revolutions reduced. At the end of the test, the solution was recovered, and placed again in the container.

Stage 4—Coating Caffeine with 40.0 kg of Solution of Shellac 30% w/w in Ethanol 96% and 32.0 kg of Talc 72.0.0 kg of the fraction between 250 and 630 microns of caffeine starting material selected in the preceding stages was placed inside an automatic rotating pan with capacity of about 200 L. Rotation of the pan was started at a speed of 6 rpm±2 rpm, 0.72 kg of talc was added and rotated for 5 minutes before starting the coating operation. The pan speed was increased to 22 rpm±2 rpm, the atomizer was positioned at about 20 cm from the rotating mass and the jet directed to the left upper quadrant, with the nebulization pressure of the atomizer adjusted to 1 bar (i.e., a range 0.8-1.2. bar). 250 g of shellac 30% w/w in ethanol 96% was sprayed over one minute and 15 seconds, and with 200.0 kg of talc sprinkled at the end. The previous operation was repeated after about two minutes and continued in the same way until 40.0 kg of solution and 32.0 kg of talc are applied on the product. The product was then dried in the pan at room temperature at a speed of 6 rpm±2 rpm for 5 hours.

Stage 5—Final Selection of the Obtained Product

The pan was rotated at a speed of 6 rpm±2 rpm, and 0.070 kg colloidal silicon dioxide was added, followed by rotating for 10 minutes. A 790 microns net was mounted on a WESTON vibrating screen, and a container mounted under the screen to collect the selected product. The screen was activated, with about 4.0 kg of coated caffeine placed on the net with a slight pressure in the direction of rotation. When all the fraction <790 microns passed through the net, the fraction >790 microns was removed and placed in a container for discarding. The preceding operation was repeated up to the end of screening to obtain the obtained product, that must then be selected with a 250 microns net. The 790 microns net was removed and the 250 microns net mounted in its place on the vibrating screen, with a container placed under the screen orifice to collect the product <250 microns. The screen was activated, with about 2.0 kg of coated caffeine placed on the net, with slight pressure in the direction of rotation.

When all the fraction <250 microns passed through the net, the product left on the net was removed and placed in the container provided for the packaging operation. The preceding operation was repeated up to the selection end, and with the fraction <250 microns discarded. The sample was then analyzed for determining titre and in vitro release rate.

Using the analysis procedure according to Example 1 supra, it was determined the product had a dissolution rate of 41.6% after 1 hour (3.00% standard deviation), 52.1% after 2 hours (3.78% standard deviation), 78.6% after 4 hours (4.16% standard deviation) and 99.8% after 8 hours (2.31% standard deviation).

Example 9

Production Process of Choline Bitartrate Taste Masked with Two Membranes

Stage 1—Selection of the Starting Material

A 790 microns net was mounted on a vibrating WESTON screen, and a container was placed under the screen orifice to collect the selected product. About 2.0 kg of choline bitartrate was placed on the net, with a slight pressure in the direction of rotation. When all of the fraction <790 microns passed through the net, the fraction >790 microns was removed and placed in a container. The preceding operation was repeated until the amount required for the production of the lot (145.0 kg+5%) was reached.

The 790 microns net was removed and a 250 microns net was mounted on the vibrating screen, with a container placed under the screen orifice to collect the selected product. About 2.0 kg of choline bitartrate was placed on the net and screened, with a slight pressure in the direction of rotation. When all the fraction <250 microns passed through the net, the product left on the net was removed and placed in a container to be stocked. The preceding operation was repeated until the amount required for the production of the lot (kg. 145.0) was reached. The fraction <250 microns was set aside.

Stage 2—Preparation of the Coating Solution 20% w/w Comprising Shellac (15%), Hydroxypropylcellulose (3%) and Ethylcellulose (2%) in Ethanol 96% (80%)

20 kg ethanol 96% was placed in a stainless steel dissolver with a capacity of about 60 L. 0.750 kg hydroxypropylcellulose was slowly added under agitation, with agitation maintained to complete dissolution (about 2 hours). Then 0.5 kg ethylcellulose and subsequently 3.750 kg shellac were added, with agitation up to complete dissolution (about 3 hours).

Stage 3—Adjustment of Flow Rate of the Coating Solution 20% w/w Comprising Shellac, Hydroxypropylcellulose and Ethylcellulose in Ethanol 96%

The solution prepared in stage 2 supra was placed in a container. A hose connected to a membrane pump was placed in the container, with the membrane pump switched on and set to a speed at 40 rpm. A container was placed to collect the solution near the atomizer nozzle, and calibrated to conduct a delivery test of one minute (theoretical amount 250 g, range 230-270 g). If the delivered quantity was below the range, increase the pump revolutions were increased, and if above the range, the revolutions reduced. At the end of the test, the solution was recovered, and placed again in the container.

Stage 4—Coating Choline Bitartrate with 25.0 kg of Solution 20% w/w Comprising Shellac, Hydroxypropylcellulose and Ethylcellulose and 25.0 kg of Talc 145.0 kg of the fraction between 250 and 790 microns of choline bitartrate starting material selected in the preceding stages was placed inside an automatic rotating pan with capacity of about 200 L. Rotation of the pan was started at a speed of 6 rpm±2 rpm, 0.5 kg of talc was added and rotated for 5 minutes before starting the coating operation. The pan speed was increased to 22 rpm±2 rpm, the atomizer was positioned at about 20 cm from the rotating mass and the jet directed to the left upper quadrant, with the nebulization pressure of the atomizer adjusted to 1 bar (i.e., a range 0.8-1.2. bar). 500 g of solution 20% w/w comprising shellac, hydroxypropylcellulose and ethylcellulose in ethanol 96% was sprayed over two minutes, and with 500 g of talc sprinkled at the end. The previous operation was repeated after about three minutes and continued in the same way until 25 kg of solution and 25 kg of talc are applied on the product. The product was then dried in the pan at room temperature at a speed of 6 rpm±2 rpm for 5 hours.

Stage 5—Final Selection of the Obtained Product

A 790 microns net was mounted on a WESTON vibrating screen, and a container mounted under the screen to collect the selected product. The screen was activated, with about 2.0 kg of coated choline bitartrate placed on the net with a slight pressure in the direction of rotation. When all the fraction <790 microns passed to through the net, the fraction >790 microns was removed and placed in a container for discarding. The preceding operation was repeated up to the end of screening to obtain the product that was then selected with a 250 microns net. The 790 microns net was removed and the 250 microns net mounted in its place on the vibrating screen, with a container placed under the screen orifice to collect the product <250 microns. The screen was activated, with about 2.0 kg of coated choline bitartrate placed on the net, with slight pressure in the direction of rotation.

When all the fraction <250 microns passed through the net, the product left on the net was removed and placed in the container provided for the packaging operation. The preceding operation was repeated up to the selection end, and with the fraction <250 microns discarded.

Stage 6—Preparation of the Coating Solution 30% w/w Comprising Shellac (30%) in Ethanol 96% (70%)

2.45 kg ethanol 96% was placed in a stainless steel dissolver with a capacity of about 5 L. 05 kg shellac was slowly added under agitation, with agitation maintained to complete dissolution (about 4 hours).

Stage 7—Adjustment of Flow Rate of the Coating Solution 30% w/w Comprising Shellac (30%) in Ethanol 96% (70%)

The solution prepared in stage 6 supra was placed in a container. A hose connected to a membrane pump was placed in the container, with the membrane pump switched on and set to a speed at 44 rpm. A container was placed to collect the solution near the atomizer nozzle, and calibrated to conduct a delivery test of one minute (theoretical amount 250 g, range 230-270 g). If the delivered quantity was below the range, the pump revolutions were increased, and if above the range, the revolutions reduced. At the end of the test, the solution was recovered, and placed again in the container.

Stage 8—Coating Choline Bitartrate with 3.50 kg of Solution 30% w/w of Shellac in Ethanol 96% and 3.50 kg of Talc The pan speed was increased to 22 rpm±2 rpm, the atomizer was positioned at about 20 cm from the rotating mass and the jet directed to the left upper quadrant, with the nebulization pressure of the atomizer adjusted to 1 bar (i.e., a range 0.8-1.2. bar). 500 g of solution of shellac 30% w/w in ethanol 96% was sprayed over five minutes, and with 500 g of talc sprinkled at the end. The previous operation was repeated after about three minutes and continued in the same way until 3.5 kg of solution and 3.5 kg of talc are applied on the product. The product was then dried in the pan at room temperature at a speed of 6 rpm±2 rpm for 8 hours.

Stage 9—Final Selection of the Obtained Product

A 790 microns net was mounted on a WESTON vibrating screen, and a container mounted under the screen to collect the selected product. The screen was activated, with about 2.0 kg of coated choline bitartrate placed on the net with a slight pressure in the direction of rotation. When all the fraction <790 microns passed through the net, the fraction >790 microns was removed and placed in a container for discarding. The preceding operation was repeated up to the end of screening to obtain the obtained product, that must then be selected with a 250 microns net. The 790 microns net was removed and the 250 microns net mounted in its place on the vibrating screen, with a container placed under the screen orifice to collect the product <250 microns. The screen was activated, with about 2.0 kg of coated choline bitartrate placed on the net, with slight pressure in the direction of rotation.

When all the fraction <250 microns passed to the lower part of the net, the product left on the net was removed and placed in the container provided for the packaging operation. The preceding operation was repeated up to the selection end, and with the fraction <250 microns discarded.

Using the analysis procedure according to Example 1 supra, it was determined the product had a dissolution rate of 100.7% after 0.5 hour (4.47% standard deviation).

Example 10

Production Process of Tribasic Potassium Citrate Monohydrate Taste Masked with Two Membranes Stage 1—Selection of the Starting Material A 790 microns net was mounted on a vibrating WESTON screen, and a container was placed under the screen orifice to collect the selected product. About 4.0 kg of potassium citrate was placed on the net, with a slight pressure in the direction of rotation. When all of the fraction <790 microns passed to the lower part of the net, the fraction >790 microns was removed and placed in a container. The preceding operation was repeated until the amount required for the production of the lot (135.0 kg+5%) was reached.

The 790 microns net was removed and a 250 microns net was mounted on the vibrating screen, with a container placed under the screen orifice to collect the selected product. About 2.0 kg of potassium citrate was placed on the net and screened, with a slight pressure in the direction of rotation. When all the fraction <250 microns passed through the net, the product left on the net was removed and placed in a container to be stocked. The preceding operation was repeated until the amount required for the production of the lot (kg. 135.0) was reached. The fraction <250 microns was set aside.

Stage 2—Preparation of the First Coating Solution 20% w/w Comprising Polyvinylpyrrolidone K 30 (20%) in Ethanol 96% (80%)

14 kg ethanol 96% was placed in a stainless steel dissolver with a capacity of about 60 L. 3.50 kg polyvinylpyrrolidone K 30 was slowly added under agitation, with agitation maintained to complete dissolution (about 2 hours).

Stage 3—Adjustment of Flow Rate of the Coating Solution 20% w/w Comprising Polyvinylpyrrolidone K 30 in Ethanol 96%

The solution prepared in stage 2 supra was placed in a container. A hose connected to a membrane pump was placed in the container, with the membrane pump switched on and set to a speed at 45 rpm. A container was placed to collect the solution near the atomizer nozzle, and calibrated to conduct a delivery test of one minute (theoretical amount 250 g, range 230-270 g). If the delivered quantity was below the range, the pump revolutions were increased, and if above the range, the revolutions reduced. At the end of the test, the solution was recovered, and placed again in the container.

Stage 4—Coating Tribasic Potassium Citrate Monohydrate with 17.5 kg of Solution 20% w/w Comprising Polyvinylpyrrolidone K 30 in Ethanol 96% and 17.50 kg of Talc 135.0 kg of the fraction between 250 and 790 microns of tribasic potassium citrate monohydrate starting material selected in the preceding stages was placed inside an automatic rotating pan with capacity of about 200 L. Rotation of the pan was started at a speed of 6 rpm±2 rpm, 0.850 kg of talc was added and rotated for 5 minutes before starting the coating operation. The pan speed was increased to 22 rpm±2 rpm, the atomizer was positioned at about 20 cm from the rotating mass and the jet directed to the left upper quadrant, with the nebulization pressure of the atomizer adjusted to 1 bar (i.e., a range 0.8-1.2. bar). 500 g of solution 20% w/w comprising polyvinylpyrrolidone K 30 in ethanol 96% was sprayed over two minutes, and with 500 g of talc sprinkled at the end. The previous operation was repeated after about three minutes and continued in the same way until 17 kg of solution and 17 kg of talc were applied on the product. The product was then dried in the pan at room temperature at a speed of 6 rpm±2 rpm for 5 hours.

Stage 5—Preparation of the Second Coating Solution 30% w/w Comprising Shellac (30%) in Ethanol 96% (70%)

13.3 kg ethanol 96% was placed in a stainless steel dissolver with a capacity of about 60 L. 5.70 kg shellac was slowly added under agitation, with agitation maintained to complete dissolution (about 4 hours).

Stage 6—Adjustment of Flow Rate of the Coating Solution 30% w/w Comprising Shellac (30%) in Ethanol 96% (70%)

The solution prepared in stage 5 supra was placed in a container. A hose connected to a membrane pump was placed in the container, with the membrane pump switched on and set to a speed at 24 rpm. A container was placed to collect the solution near the atomizer nozzle, and calibrated to conduct a delivery test of one minute (theoretical amount 150 g, range 145-155 g). If the delivered quantity was below the range, the pump revolutions were increased, and if above the range, the revolutions reduced. At the end of the test, the solution was recovered, and placed again in the container.

Stage 7—Coating Tribasic Potassium Citrate Monohydrate with 19.0 kg of Solution 30% w/w of Shellac in Ethanol 96% and 19 kg of Talc A pan was rotated at a speed of 22 rpm±2 rpm, an atomizer was positioned at about 20 cm from the rotating mass and the jet directed to the left upper quadrant, with the nebulization pressure of the atomizer adjusted to 1 bar (i.e., a range 0.8-1.2. bar). 300 g of solution of shellac 30% w/w in ethanol 96% was sprayed over two minutes, and with 300 g of talc sprinkled at the end. The previous operation was repeated after about three minutes and continued in the same way until 19 kg of solution and 19 kg of talc were applied on the product. The product was then dried in the pan at room temperature at a speed of 6 rpm±2 rpm for 8 hours.

Stage 8—Final Selection of the Obtained Product

A 790 microns net was mounted on a WESTON vibrating screen, and a container mounted under the screen to collect the selected product. The screen was activated, with about 4.0 kg of coated potassium citrate placed on the net with a slight pressure in the direction of rotation. When all the fraction <790 microns passed through the net, the fraction >790 microns was removed and placed in a container for discarding. The preceding operation was repeated up to the end of screening to obtain the obtained product, that was then selected with a 250 microns net. The 790 microns net was removed and the 250 microns net mounted in its place on the vibrating screen, with a container placed under the screen orifice to collect the product <250 microns. The screen was activated, with about 2.0 kg of coated potassium citrate placed on the net, with slight pressure in the direction of rotation.

When all the fraction <250 microns passed through the net, the product left on the net was removed and placed in the container provided for the packaging operation. The preceding operation was repeated up to the selection end, and with the fraction <250 microns discarded.

The particles of potassium citrate coated with shellac where then analyzed for dissolution according to experimental protocol according to Example 1 supra. Three batches of coated potassium citrate were analyzed: the first batch, having a titre of 44.1 mg., exhibited a dissolution rate of 32.3% after 2 minutes (11.16% standard deviation), 82.1% after 10 minutes (5.71% standard deviation) and 94.5% after 30 minutes (1.11% standard deviation); the second batch, having a titre of 41.0 mg., exhibited a dissolution rate of 36.9% after 2 minutes, 87.5% after 10 minutes and 96.3% after 30 minutes; and the third batch, having a titre of 40.1 mg., exhibited a dissolution rate of 29.7% after 2 minutes, 79.8% after 10 minutes and 94.4% after 30 minutes.

Example 11

Production Process of L-Methionine Taste Masked with Two Layers of the Same Membrane Stage 1—Selection of the Starting Material A 790 microns net was mounted on a vibrating WESTON screen, and a container was placed under the screen orifice to collect the selected product. About 4.0 kg of L-methionine was placed on the net, with a slight pressure in the direction of rotation. When all of the fraction <790 microns passed through the net, the fraction >790 microns was removed and placed in a container. The preceding operation was repeated until the amount required for the production of the lot (140.0 kg+5%) was reached.

The 790 microns net was removed and a 125 microns net was mounted on the vibrating screen, with a container placed under the screen orifice to collect the selected product. About 2.0 kg of L-methionine was placed on the net and screened, with a slight pressure in the direction of rotation. When all the fraction <125 microns passed through the net, the product left on the net was removed and placed in a container to be stocked. The preceding operation was repeated until the amount required for the production of the lot (140.0 kg.) was reached. The fraction <125 microns was set aside.

Stage 2—Preparation of the Coating Solution 20% w/w Comprising Shellac (15%) and Ethylcellulose (5%) in Ethanol 96% (80%)

39.2 kg ethanol 96% was placed in a stainless steel dissolver with a capacity of about 60 L. 2.45 kg ethylcellulose was slowly added under agitation, with agitation maintained to complete dissolution (about 4 hours). 7.35 kg shellac was then added under agitation up to complete dissolution (about 3 hours).

Stage 3—Adjustment of Flow Rate of the Coating Solution 20% w/w Comprising Shellac and Ethylcellulose in Ethanol 96%

27.0 kg of the solution prepared in stage 2 supra was placed in a container. A hose connected to a membrane pump was placed in the container, with the membrane pump switched on and set to a speed at 45 rpm. A container was placed to collect the solution near the atomizer nozzle, and calibrated to conduct a delivery test of one minute (theoretical amount 250 g, range 230-270 g). If the delivered quantity was below the range, increase the pump revolutions were increased, and if above the range, the revolutions reduced. At the end of the test, the solution was recovered, and placed again in the container.

Stage 4—Coating L-Methionine with 27.0 kg of Solution 20% w/w Comprising Shellac and Ethylcellulose in Ethanol 96% and 16.2 kg of Talc 140.0 kg of the fraction between 250 and 790 microns of L-methionine starting material selected in the preceding stages was placed inside an automatic rotating pan with capacity of about 200 L. Rotation of the pan was started at a speed of 6 rpm±2 rpm, 1.0 kg of talc was added and rotated for 5 minutes before starting the coating operation. The pan speed was increased to 22 rpm±2 rpm, the atomizer was positioned at about 20 cm from the rotating mass and the jet directed to the left upper quadrant, with the nebulization pressure of the atomizer adjusted to 1 bar (i.e., a range 0.8-1.2. bar). 500 g of solution 20% w/w comprising shellac and ethylcellulose in ethanol 96% was sprayed over two minutes, and with 300 g of talc sprinkled at the end. The previous operation was repeated after about three minutes and continued in the same way until 27 kg of solution and 16.2 kg of talc are applied on the product. The product was then dried in the pan at room temperature at a speed of 6 rpm±2 rpm for 5 hours.

Stage 5—First Selection

A 910 microns net was mounted on a WESTON vibrating screen, and a container mounted under the screen to collect the selected product. The screen was activated, with about 4.0 kg of coated L-methionine placed on the net with a slight pressure in the direction of rotation. When all the fraction <910 microns passed through the net, the fraction >910 microns was removed and placed in a container for discarding. The preceding operation was repeated up to the end of screening to obtain the product that was then selected with a 125 microns net. The 910 microns net was removed and the 125 microns net mounted in its place on the vibrating screen, with a container placed under the screen orifice to collect the product <125 microns. The screen was activated, with about 2.0 kg of coated L-methionine placed on the net, with slight pressure in the direction of rotation.

When all the fraction <125 microns passed through the net, the product left on the net was removed and placed in the container provided for the packaging operation. The preceding operation was repeated up to the selection end, and with the fraction <125 microns discarded.

Stage 6—Second Coating L-Methionine with 22.0 kg of Solution 20% w/w Comprising Shellac and Ethylcellulose in Ethanol 96% and 13.2 kg of Talc The pan speed was rotated at 22 rpm±2 rpm, the atomizer was positioned at about 20 cm from the rotating mass and the jet directed to the left upper quadrant, with the nebulization pressure of the atomizer adjusted to 1 bar (i.e., a range 0.8-1.2. bar). 500 g of solution 20% w/w comprising shellac and ethylcellulose in ethanol 96% was sprayed over two minutes, and with 300 g of talc sprinkled at the end. The previous operation was repeated after about three minutes and continued in the same way until 22 kg of solution and 13.2 kg of talc are applied on the product. The product was then dried in the pan at room temperature at a speed of 6 rpm±2 rpm for 8 hours.

Stage 7—Final Selection of the Obtained Product

A 910 microns net was mounted on a WESTON vibrating screen, and a container mounted under the screen to collect the selected product. The screen was activated, with about 4.0 kg of coated L-methionine placed on the net with a slight pressure in the direction of rotation. When all the fraction <910 microns passed through the net, the fraction >910 microns was removed and placed in a container for discarding. The preceding operation was repeated up to the end of screening to obtain the product that was then selected with a 125 microns net. The 910 microns net was removed and the 125 microns net mounted in its place on the vibrating screen, with a container placed under the screen orifice to collect the product <125 microns. The screen was activated, with about 2.0 kg of coated L-methionine placed on the net, with slight pressure in the direction of rotation.

When all the fraction <125 microns passed through the net, the product left on the net was removed and placed in the container provided for the packaging operation. The preceding operation was repeated up to the selection end, and with the fraction <125 microns discarded.

Example 12

Production Process of Methylsulfonylmethane Taste Masked with Two Membranes

Stage 1—Selection of the Starting Material

A 790 microns net was mounted on a vibrating WESTON screen, and a container was placed under the screen orifice to collect the selected product. About 4.0 kg of methylsulfonylmethane was placed on the net, with a slight pressure in the direction of rotation. When all of the fraction <790 microns passed through the net, the fraction >790 microns was removed and placed in a container. The preceding operation was repeated until the amount required for the production of the lot (157.5 kg+20%) is reached.

The 790 microns net was removed and a 250 microns net was mounted on the vibrating screen, with a container placed under the screen orifice to collect the selected product. About 2.0 kg of methylsulfonylmethane was placed on the net and screened, with a slight pressure in the direction of rotation. When all the fraction <250 microns passed through the net, the product left on the net was removed and placed in a container to be stocked. The preceding operation was repeated until the amount required for the production of the lot (kg. 157.5) was reached. The fraction <250 microns was set aside.

Stage 2—Preparation of the First Coating Solution 20% w/w Comprising Polyvinylpyrrolidone K 30 (20%) in Ethanol 96% (80%)

2.56 kg ethanol 96% was placed in a stainless steel dissolver with a capacity of about 60 L. 0.640 kg polyvinylpyrrolidone K 30 was slowly added under agitation, with agitation maintained to complete dissolution (about 2 hours).

Stage 3—Adjustment of Flow Rate of the Coating Solution 20% w/w Comprising Polyvinylpyrrolidone K 30 in Ethanol 96%

The solution prepared in stage 2 supra was placed in a container. A hose connected to a membrane pump was placed in the container, with the membrane pump switched on and set to a speed at 45 rpm. A container was placed to collect the solution near the atomizer nozzle, and calibrated to conduct a delivery test of one minute (theoretical amount 200 g, range 180-220 g). If the delivered quantity was below the range, increase the pump revolutions were increased, and if above the range, the revolutions reduced. At the end of the test, the solution was recovered, and placed again in the container.

Stage 4—Coating Methylsulfonylmethane with 3.2 kg of Solution 20% w/w Comprising Polyvinylpyrrolidone K 30 in Ethanol 96% and 2.240 kg of Talc 135.0 kg of the fraction between 250 and 790 microns of methylsulfonylmethane starting material selected in the preceding stages was placed inside an automatic rotating pan with capacity of about 200 L. Rotation of the pan was started at a speed of 6 rpm±2 rpm, 1.250 kg of talc was added and rotated for 5 minutes before starting the coating operation. The pan speed was increased to 22 rpm±2 rpm, the atomizer was positioned at about 20 cm from the rotating mass and the jet directed to the left upper quadrant, with the nebulization pressure of the atomizer adjusted to 1 bar (i.e., a range 0.8-1.2. bar). 200 g of solution 20% w/w comprising polyvinylpyrrolidone K 30 in ethanol 96% was sprayed over two minutes, and with 140 g of talc sprinkled at the end. The previous operation was repeated after about three minutes and continued in the same way until 3.2 kg of solution and 2.240 kg of talc are applied on the product. The product was then dried in the pan at room temperature at a speed of 6 rpm±2 rpm for 5 hours.

Stage 5—Preparation of the Second Coating Solution 30% w/w Comprising Shellac (30%) in Ethanol 96% (70%)

11.70 kg ethanol 96% was placed in a stainless steel dissolver with a capacity of about 60 L. 5.0 kg shellac was slowly added under agitation, with agitation maintained to complete dissolution (about 4 hours).

Stage 6—Adjustment of Flow Rate of the Coating Solution 30% w/w Comprising Shellac in Ethanol 96% (70%)

The solution prepared in stage 5 supra was placed in a container. A hose connected to a membrane pump was placed in the container, with the membrane pump switched on and set to a speed at 40 rpm. A container was placed to collect the solution near the atomizer nozzle, and calibrated to conduct a delivery test of one minute (theoretical amount 250 g, range 230-270 g). If the delivered quantity was below the range, increase the pump revolutions were increased, and if above the range, the revolutions reduced. At the end of the test, the solution was recovered, and placed again in the container.

Stage 7—Coating Methylsulfonylmethane with 16.70 kg of Solution 30% w/w of Shellac in Ethanol 96% and 16.7 kg of Talc A pan was rotated at a speed of 22 rpm±2 rpm, an atomizer was positioned at about 20 cm from the rotating mass and the jet directed to the left upper quadrant, with the nebulization pressure of the atomizer adjusted to 1 bar (i.e., a range 0.8-1.2. bar). 250 g of solution of shellac 30% w/w in ethanol 96% was sprayed over one minute, and with 250 g of talc sprinkled at the end. The previous operation was repeated after about three minutes and continued in the same way until 16.7 kg of solution and 16.7 kg of talc were applied on the product. The product was then dried in the pan at room temperature at a speed of 6 rpm±2 rpm for 8 hours.

Stage 8—Final Selection of the Obtained Product

A 790 microns net was mounted on a WESTON vibrating screen, and a container mounted under the screen to collect the selected product. The screen was activated, with about 4.0 kg of coated methylsulfonylmethane placed on the net with a slight pressure in the direction of rotation. When all the fraction <790 microns passed through the net, the fraction >790 microns was removed and placed in a container for discarding. The preceding operation was repeated up to the end of screening to obtain the product that was then selected with a 250 microns net. The 790 microns net was removed and the 250 microns net mounted in its place on the vibrating screen, with a container placed under the screen orifice to collect the product <250 microns. The screen was activated, with about 2.0 kg of coated methylsulfonylmethane placed on the net, with slight pressure in the direction of rotation.

When all the fraction <250 microns passed through the net, the product left on the net was removed and placed in the container provided for the packaging operation. The preceding operation was repeated up to the selection end, and with the fraction <250 microns discarded.

Example 13

Production Process of Coated Granules of Caffeine Taste Masked with Shellac in a Fluidized Bed 662 g. of caffeine granules of 660-800 microns in size were weighed on a precision balance and then transferred to a fluidized bed (GPCG 1.1, Glatt (D)) equipped with a rotor insert (5 liter capacity), 1.2 mm. spray nozzle, peristaltic pump (flocon 1003) and gravity feeder (1 liter capacity). In a glass cylinder, 1200 ml of 20% water dispersion of shellac ammonium salt was measured and transferred to a volumetric flask connected to the gravity feeder and then placed on a precision balance to follow amount delivered over time (g/min). 302 g. of micronized talc of 5-30 microns in size was weighed and transferred to the gravity feeder to delivery the following amount. The rotor disk was switched on at 693 rpm and a constant flow volume of air started and equal to 75 $m^3$/hour at 27° C.

After the granules of caffeine had been fluidized for 7 minutes, the pump was activated to deliver the aqueous shellac dispersion at a rate of 25 g/min with an atomizing pressure of 2 bar; and after 2 minutes, the gravity feeder was activated to deliver the talc at a rate of 10 g/min. After 48 minutes, the shellac dispersion had been entirely sprayed along with all the talc. Then, the coated particles were kept in motion at the same rotor speed and dried for 23 minutes at 50° C.

Using the analysis procedure set forth in Example 2 supra, it was determined the product had a dissolution rate of 80.2% after 1 hour (20.55% standard deviation), 85.6% after 2 hours (9.61% standard deviation), 90.1% after 4 hours (3.30% standard deviation) and 92.2% after 8 hours (1.89% standard deviation).

Additional Preparations

In accordance with the procedures set forth supra, it is also possible to coat (1) capsicum granules with a first coating of 30% shellac in 70% ethanol 96% and talc and a second coating of 25% shellac in 75% purified water and talc, (2) rhodiola rosea granules with a first coating of 80% ethanol 96% containing 15% shellac, 3% hydroxypropylcellulose, 2% ethylcellulose and talc and a second coating of 30% shellac in 70% ethanol 96% and talc, and (3) magnesium sulfate granules with a first coating of 80% ethanol 96% containing 15% shellac, 3% hydroxypropylcellulose, 2% ethylcellulose and talc, and a second coating of 30% shellac in 70% ethanol 96% and talc Finally it is to be pointed out that many variations, additions and/or substitutions may be resorted to the polymeric matrix, more particularly concerning the nature of polymers used as a function of the kind of modified release to be obtained and its method of production, without departing however from its characteristics nor falling out of its scope of protection, as defined in the appended claims.

The invention claimed is:

1. A polymeric matrix for oral administration with modified release, comprising
    coated particles of active substance its the form of powder,
    the particles being directly covered with a release regulating membrane as the coating, wherein
    inert cores or supports in the particles are eliminated,
    the particles each have a core composed of only the active substance and omitting all inert substances,
    the coated particles have a size, together with the coating thereon, between about 790 microns and about 425 microns,
    the active substance is thioctic acid, and
    the release regulating membrane comprises shellac and optionally further comprises talc and/or maize starch.

2. The polymeric matrix of claim 1, wherein the release regulating membrane comprises a solution of shellac in ethanol and talc.

3. A polymeric matrix for oral administration with modified release, comprising
- coated particles of active substance in the form of powder,
- the particles being directly covered with a release regulating membrane as the coating, wherein
- inert cores or supports in the particles are eliminated,
- the particles each have a core composed of only the active substance and omitting all inert substances,
- the coated panicles have a size, together with the coating thereon, between about 790 microns and about 425 microns,
- the active substance is selected from at least one of caffeine, choline bitartrate, potassium citrate, L-methionine and methylsulfonylmethane, and
- the release regulating membrane comprises ethylcellulose, hydroxypropyl cellulose or polyvinylpyrrolidone, and optionally further comprises talc and/or maize starch.

4. The polymeric matrix of claim 3, wherein the matrix blended with excipients is compressed directly to obtain tablets with immediate disintegration.

5. The polymeric matrix according of claim 3, wherein the matrix is blended with flavoring and other excipients masking the taste of the active substance, for a better compliance of users.

6. The matrix of claim 3, wherein weight ratio of active core to coating in each granule is from about 6:1 to about 1:1.

7. The matrix of claim 6, wherein weight ratio of active core to coating in each granule is from about 3:1 to about 1:1.

8. The matrix of claim 7, wherein weight ratio of active core to coating in each granule is from about 2:1 to about 1:1.

9. A method for preparing a homogeneous and uniform extemporaneous suspension in educed amount of liquid, comprising the step of incorporating the matrix of claim 3 into said suspension.

10. A method for preparing hard gelatine capsules, comprising the step of incorporating the matrix of claim 3 into said hard gelatine capsules.

11. A method for preparing single dose oral soluble sachets, comprising the step of incorporating the matrix of claim 3 into said sachets.

12. A method of preparing the polymeric matrix with modified release according to claim 3, comprising the steps of:
- charging in a rotating pan a starting material comprising the active substance with particle size between 200 and 700 µm;
- rotating the pan directly covering the particle of the active substance in one or more stages with one or more layers of the release regulating polymeric membrane;
- at the end of the covering step, sieving the product with a mesh of 790 µm and dusting with a mesh of 425 µm; and
- drying the product in the pan at room temperature.

13. The method according to claim 12, wherein the polymeric matrix is blended with excipients to make disintegrating tablets and single dose oral soluble sachets.

14. The method according to claim 12, wherein the polymeric matrix is blended with flavoring and other excipients for masking the taste of the active substance.

15. The method according to claim 12, wherein two or more active substances are mixed for a combination therapy or food integration.

* * * * *